United States Patent
Shimp

(10) Patent No.: US 9,539,363 B2
(45) Date of Patent: Jan. 10, 2017

(54) COLLAGEN MATRIX

(71) Applicant: Warsaw Orthopedic, Inc., Warsaw, IN (US)

(72) Inventor: Lawrence A. Shimp, Burlington, WI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/260,430

(22) Filed: Apr. 24, 2014

(65) Prior Publication Data

US 2015/0306276 A1   Oct. 29, 2015

(51) Int. Cl.
| | |
|---|---|
| *A61L 27/46* | (2006.01) |
| *A61L 27/24* | (2006.01) |
| *A61L 27/54* | (2006.01) |
| *A61L 27/58* | (2006.01) |
| *C08L 89/06* | (2006.01) |

(52) U.S. Cl.
CPC ............... *A61L 27/24* (2013.01); *A61L 27/46* (2013.01); *A61L 27/54* (2013.01); *A61L 27/58* (2013.01); *A61L 2300/414* (2013.01); *A61L 2430/02* (2013.01)

(58) Field of Classification Search
CPC .......... A61P 19/00; A61K 47/48; A61K 38/39
See application file for complete search history.

(56) References Cited

U.S. PATENT DOCUMENTS

| | | |
|---|---|---|
| 4,140,537 A | 2/1979 | Luck et al. |
| 4,863,732 A | 9/1989 | Nathan et al. |
| 4,888,366 A | 12/1989 | Chu et al. |
| 5,073,378 A | 12/1991 | Shoshan et al. |
| 5,677,284 A | 10/1997 | Li |
| 8,114,428 B2 | 2/2012 | Briest |
| 2006/0286144 A1 | 12/2006 | Yang et al. |
| 2010/0016872 A1* | 1/2010 | Bayon ............... A61F 2/0063 606/151 |
| 2010/0196489 A1 | 8/2010 | Thorne |
| 2012/0195952 A1* | 8/2012 | King ..................... A61K 31/00 424/426 |

OTHER PUBLICATIONS

Lee et al. (International Journal of Pharmaceutics. 2001;221:1-22).*
Roeder et al. (Transactions of the ASME 2002;124:214-222).*
Chen et al. (Biomaterials 2005; 26:2559-2566).*
Dai et al. (Biomaterials 2010;31:2141-2152).*

* cited by examiner

*Primary Examiner* — Ernst V Arnold
(74) *Attorney, Agent, or Firm* — Sorell Lenna & Schmidt LLP

(57) ABSTRACT

Methods for making a biodegradable collagen matrix having increased osteoinductivity and a biodegradable collagen matrix prepared by these methods are provided. In various embodiments, the methods include providing an acidic collagen slurry and mixing it with at least one water soluble and/or hydrophilic bioactive agent under conditions sufficient to cause the collagen slurry to self-assemble into macroscopic collagen fibers and cause the at least one bioactive agent to form a collagen matrix containing the bioactive agent. Conditions sufficient to cause the collagen slurry to self-assembly include raising the pH of the slurry to from about 5 to about a pH of 9 and/or adding bone powder, calcium phosphate, hydroxyapatite, DBM or a mixture thereof to the acidic collagen slurry in order to raise the pH from about 5 to about 9.

12 Claims, No Drawings

COLLAGEN MATRIX

BACKGROUND

Many effective growth factors and other bioactive agents have been developed to help in tissue repair and in treating diseases by applying them to a localized area, such as a surgical site. Conventional methods of delivering growth factors and/or other bioactive agents utilize many types of drug delivery technologies.

Current drug delivery technologies utilize different carriers such as polymeric matrices, microencapsulation, or collagen sponges. In general, polymeric matrix or microencapsulation techniques require the incorporation of the bioactive agent into a carrier at a production facility. While release characteristics can be usually controlled, generally the materials used for carriers fail to promote tissue repair and growth.

Collagen sponges are frequently used as scaffolds for tissue growth, but normally the bioactive agent is added to the sponge at the point of use. In nature, a bioactive agent such as bone morphogenic proteins are found bound to collagen. Although, collagen is a very good carrier for bone morphogenic proteins, when bone morphogenic proteins are added to collagen sponges, the original bonding found in nature is not recreated and, as a result the bone morphogenic proteins are only physically incorporated in the collagen sponges and become released too quickly, thereby failing to retain their full efficacy.

Sometimes when the surgeon manipulates the matrix to place it in the bone defect, excessive amounts of growth factor (e.g., bone morphogenic protein) may leak or migrate from the matrix, which may reduce a stable microenvironment for new bone and/or cartilage growth. This migration of the bioactive agent may also cause the collagen sponge to fail to retain its full efficacy over time to maximally promote bone and/or cartilage growth at a target site, side effects can be exaggerated and dosages required for treatment become uneconomically large.

Thus, there is a need to develop new osteogenic compositions and methods that improve bone and/or cartilage repair by retaining bone morphogenic proteins and other growth factors much longer than prior art collagen sponges. It is, therefore, desirable to provide methods of preparing bone material having increased surface area, increased biological activities including but not limited to osteoinductive activity. Further, it is also desirable to provide bone implants prepared from bone material having enhanced osteoinductivity and enhanced ability to grow and integrate into a host bone.

SUMMARY

Methods for making a biodegradable collagen matrix having increased osteoinductivity are provided. In various embodiments, the methods include providing an acidic collagen slurry which is mixed with at least one water soluble and/or hydrophilic bioactive agent under conditions sufficient to cause the collagen slurry to self-assemble into macroscopic collagen fibers and cause the at least one bioactive agent to form a collagen matrix containing the bioactive agent. Conditions sufficient to cause the collagen slurry to self-assembly include raising the pH of the slurry to from about 5 to about a pH of 9; and/or adding bone powder, calcium phosphate, hydroxyapatite, DBM or a mixture thereof to the acidic collagen slurry in order to raise the pH from about 5 to about 9.

In other embodiments, the method for making a biodegradable collagen matrix having increase osteoinductivity includes adding a dried mixture of a bioactive agent and bone powder, calcium phosphate, hydroxyapatite, DBM or a mixture thereof to an acidic collagen slurry to form a collagen matrix of macroscopic collagen fibers wherein the bioactive agent is bound to the macroscopic collagen fibers. In some embodiments, the method for making a biodegradable collagen matrix further includes removing water from the collagen matrix containing the bioactive agent. In yet other embodiments, the method for making a biodegradable collagen matrix further comprises adding glycerol to the dried collagen matrix to form a malleable complex that does not harden. In various other embodiments, the dried mixture of a bioactive agent and bone powder, calcium phosphate, hydroxyapatite, DBM or a mixture thereof is added to the acidic collagen slurry prior to use at a surgical site by a medical professional.

The present application also provides a biodegradable collagen matrix for delivery of a bioactive agent. The collagen matrix includes a plurality of macroscopic collagen fibers comprising the bioactive agent bound to the macroscopic collagen fibers and is precipitated from an acidic collagen slurry by causing the pH of the slurry to be raised above a pH from about 5 to about a pH of 9.

In certain embodiments, the bioactive agent bound onto the macroscopic fibers of the collagen matrix comprise a growth factor, a bone morphogenetic protein, an analgesic, an anti-inflammatory, and antibiotic, a cytokine, a chemotherapeutic or a mixture thereof In some embodiments, the bone morphogenetic protein bound to the macroscopic fibers of the collagen matrix can be BMP-2.

In other embodiments, a biodegradable collagen matrix for delivery of a bioactive agent is provided, wherein the collagen matrix comprises a plurality of macroscopic collagen fibers having the bioactive agent bound to the macroscopic collagen fibers. In these embodiments, the collagen matrix has a structure that results from reacting an acidic collagen slurry or suspension with at least one water soluble and/or hydrophilic bioactive agent so as to raise the pH of the slurry above 5 to about 9 sufficient to cause the collagen slurry to self-assemble into a collagen matrix of macroscopic collagen fibers.

In other embodiments, the methods described herein contemplate further adding an osteoinductive additive comprising bone marrow aspirant, blood, blood products, synthetic and naturally-derived bone morphogenic proteins, growth factors, particulate demineralized bone matrix, or mixtures thereof In other embodiments, the methods described herein contemplate further adding an osteoconductive additive, the osteoconductive additive comprising calcium phosphates, calcium sulfate, particulate demineralized bone matrix, naturally-derived allogenic bone mineral, naturally-derived autogenic bone mineral or mixtures thereof.

In one embodiment, there is a biodegradable collagen matrix for delivery of a bioactive agent, the collagen matrix comprising a plurality of macroscopic collagen fibers comprising the bioactive agent bound to the macroscopic collagen fibers, wherein the collagen matrix has a structure that results from reacting an acidic collagen slurry (e.g., collagen suspension) with at least one water soluble and/or hydrophilic bioactive agent so as to raise the pH of the slurry above 5 to about 9 sufficient to cause the collagen slurry to self-assemble into a collagen matrix of macroscopic collagen fibers.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the detailed description is to be regarded as illustrative in nature and not restrictive.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

"Bioactive agent" or "bioactive compound" is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In certain embodiments, the bioactive agent is a small molecule. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD.

A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 2013; and the United States Pharmacopeia-37/National Formulary-32, published by the United States Pharmacopeia Convention, Inc., Rockville Md., 2014, all of which are incorporated herein by reference. Drugs for human use listed by the U.S. Food and Drug Administration (FDA) under 21 C.F.R. §§330.5, 331 through 361, and 440 hrough 460, and drugs for veterinary use listed by the FDA under 21 C.F.R. §§500 through 589, all of which are incorporated herein by reference, are also considered acceptable for use in accordance with the present invention.

"Biodegradable", "bioerodable", or "resorbable" materials are materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Biodegradable materials also include materials that are broken down within cells. Degradation may occur by hydrolysis, enzymatic processes, phagocytosis, or other processes.

"Biocompatible," as used herein, is intended to describe materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, for example, bone tissue. In certain embodiments, the demineralized compositions described herein include preparations containing less than 5% calcium. "Demineralized" is intended to encompass such expressions as "substantially demineralized," "partially demineralized," "surface demineralized," and "fully demineralized." "Partially demineralized" is intended to encompass "surface demineralized."

"Demineralized bone activity" refers to the osteoinductive activity of demineralized bone.

"Demineralized bone matrix (DBM)," as used herein, refers to any material generated by removing mineral material from bone tissue. In some embodiments, the DBM compositions as used herein include preparations containing less than 5% calcium and, in some embodiments, less than 1% calcium by weight. In other embodiments, the DBM compositions comprise partially demineralized bone (e.g., preparations with greater than 5% calcium by weight but containing less than 100% of the original starting amount of calcium).

The term "lyophilized" or "freeze-dried" includes a state of a substance that has been subjected to a drying procedure such as lyophilization, where at least 50% of moisture has been removed. The growth factor may be lyophilized or freeze-dried.

"Mammal," as used herein refers to organisms from the taxonomy class "mammalian," including but not limited to humans, other primates such as chimpanzees, apes, orangutans and monkeys, rats, mice, cats, dogs, cows, or horses.

"Osteoconductive," as used herein, refers to the ability of a substance to serve as a template or substance along which bone may grow.

"Osteogenic," as used herein, refers to materials containing living cells capable of differentiation into bone tissue.

"Osteoimplant," as used herein, refers to any implant prepared in accordance with the embodiments described herein and therefore may include expressions such as bone material, bone membrane, bone graft.

"Osteoinductive," as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

A "therapeutically effective amount" or "effective amount" is such that when administered, the drug results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

The terms "treating" and "treatment" when used in connection with a disease or condition refer to executing a protocol that may include osteochondral repair procedure, administering one or more drugs to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the osteogenic composition can be used to treat subchondral, osteochondral, hyaline cartilage and/or condyle defects.

Collagen Matrix and Methods of Preparation

In various aspects, a biodegradable collagen matrix for delivery of a bioactive agent is provided. The collagen matrix comprises a plurality of macroscopic collagen fibers having the bioactive agent bound to the macroscopic collagen fibers, the collagen matrix precipitated from an acidic collagen slurry by causing the pH of the slurry to be raised above a pH from about 5 to about a pH of 9.

In other embodiments, a biodegradable collagen matrix for delivery of a bioactive agent is provided wherein the collagen matrix comprises a plurality of macroscopic collagen fibers comprising the bioactive agent bound to the macroscopic collagen fibers. In these embodiments, the collagen matrix has a structure that results from reacting an acidic collagen slurry or suspension with at least one water soluble and/or hydrophilic bioactive agent so as to raise the pH of the slurry above 5 to about 9, which is sufficient to cause the collagen slurry to self-assemble into a collagen matrix of macroscopic collagen fibers.

In one embodiment, the present application provides a method for making a biodegradable collagen matrix. The method includes providing an acidic collagen slurry or suspension, and mixing the slurry or suspension with at least one water soluble or hydrophilic bioactive agent under conditions sufficient to cause the collagen slurry to self-assemble into macroscopic collagen fibers and cause the at least one bioactive agent to form a collagen matrix wherein the bioactive agent becomes uniformly distributed. Conditions sufficient to cause the collagen slurry to self-assembly comprise raising the pH of the slurry to from about 5 to about a pH of 9 and/or adding bone powder, calcium phosphate, hydroxyapatite, DBM or a mixture thereof to the slurry to raise the pH from about 5 to about 9.

In some embodiments, collagen suspensions or slurries are made by breaking down collagen bearing tissues into small pieces and mixing them into an acid solution which results in a stable suspension or slurry. In some embodiments, in an acidic environment, as the pH is raised, collagen molecules react and bond with each other by displacing water to form collagen precipitates which self-assemble into a collagen matrix in the absence of a cross-linking agent.

In other embodiments, in an acidic environment, the collagen molecules can also react with other soluble or hydrophilic materials having negatively charged surface groups such as compounds containing hydroxides or amines. Materials capable of forming negatively charged surface groups such as hydroxides or amines comprise without limitations bioactive agents or bone particles, demineralized bone particles, calcium phosphates that can then react with the collagen molecules to bind and/or adhere to the macroscopic fibers of the collagen matrix. In some embodiments, the binding between the bioactive agent (e.g., water soluble and /or hydrophilic bioactive agent, such as for example, a growth factor, BMP, analgesic, anti-inflammatory agent, antibiotic, cytokine, chemotherapeutic agent, etc.) can be electrostatic interactions, hydrogen bonding, van der Waals interaction, hydrophobic interaction, hydrophilic interaction, covalent bonding, or non-covalent bonding.

Hydrophilic growth factors are protein based bioactive agents which are capable of binding to the collagen suspensions. In various embodiments, the growth factor(s) can be added to the acidic collagen slurry before the slurry or suspension is neutralized and precipitated. The growth factor(s) will then be incorporated chemically into the resulting collagen matrix, or into a collagen matrix that includes another substance such as bone, DBM, or calcium phosphates. The resulting collagen matrix will release the growth factor more slowly than if it were added to a fully formed collagen sponge, membrane, or composite.

Upon neutralization, namely as the pH is raised above 5 to about 9, the collagen slurry is destabilized and the collagen spontaneously assembles into macroscopic fibers. The precipitation of collagen or collagen complexes is accompanied by the release of free water because the water bonding sites on the collagen are now binding to chemically similar to water sites on the complexing material. Further evidence of a chemical interaction in the collagen precipitation is provided by the observation that the precipitated collagen complexes, when physically pulled apart, cannot recombine to form a material with the original degree of cohesiveness.

In some embodiments, to ensure greater storage stability, the water formed during the formation of the collagen matrix can be removed, and the collagen matrix can be dried prior to use, for example by lyophilization. In other embodiments, if a malleable collagen matrix is desired which does not harden, then before use without the need for rehydration, a suitable liquid such as glycerol can be added to the wet bioactive agent —collagen complex before lyophilization. Lyophilization will then remove the water but leave the added glycerol liquid. The added glycerol should be chosen based on its ability to preserve, or at least not degrade, the bioactive agent.

In other embodiments, the collagen matrix of this application can be prepared by other methods. In one aspect, the biodegradable collagen matrix is prepared by adding a dried mixture of a bioactive agent and bone powder, calcium phosphate, hydroxyapatite, DBM or a mixture thereof to an acidic collagen slurry to form a collagen matrix of macroscopic collagen fibers wherein the bioactive agent is bound to the macroscopic collagen fibers and uniformly distributed therein. In this aspect, the resulting collagen matrix will release the bioactive agent more slowly than if it were added to a fully formed collagen sponge, membrane or composite. Therefore, the bioactive agent is reacted with the forming collagen matrix structure and the structure of the matrix results from its reaction with the bioactive agent during collagen matrix formation.

As with other methods described herein, to ensure greater storage stability, the water formed during the formation of the collagen matrix can be removed, and the collagen matrix can be dried prior to use, for example by lyophilization. In other embodiments, if a malleable collagen matrix is desired which does not harden, then before use and without the need for rehydration, a suitable liquid such as glycerol can be added to the wet bioactive agent—collagen complex before lyophilization. Lyophilization will then remove the water but leave the added glycerol liquid. In some embodiments, the dried mixture of bioactive agent and bone powder, calcium phosphate, hydroxyapatite, DBM or a mixture thereof can be added to the acidic collagen slurry at the point of use, or earlier, if desired by the appropriate medical professional.

In various aspects, the biodegradable collagen matrix obtained by the methods of this application comprises, consists essentially of, or consists of macroscopically visible collagen fiber, namely, collagen fibers visible with the naked eye to which is bonded a bioactive agent uniformly distributed therein. The mean length of the collagen fibers is generally from about 3 to about 30 mm, in some embodiments, from about 5 to about 25 mm, and, in other embodiments, from about 7.5 to about 20 mm.

There are many advantages to the collagen matrices containing the bioactive agent prepared by the methods described herein. It has been unexpectedly found, that these collagen matrices mimic the natural delivery of many bioactive agents and especially growth factors to a bone defect site. Moreover, these collagen matrices can act as a scaffold for tissue growth and are fully resorbable and/or remodelable and exhibit excellent biocompatibility with all tissues.

Collagen

The collagen in the collagen matrix of this application can be derived from any collagen bearing tissue from an animal. The collagen can be allogenic or xenogenic. The collagen can be from skin, tendon, fascia, ligament, trachea, organ collagen, etc. In certain embodiments, the collagen is human collagen or other mammalian collagen (e.g., porcine, bovine, or ovine). The collagen can be sourced from any animal.

If human sourced collagen is used, some of the common processing steps, designed to remove immunogenic proteins, can optionally be skipped. Steps to remove immune proteins typically include treatment with a protolytic enzyme such as papen, or ficin, treatment with a strong oxidizing agent such as sodium chlorate, and exposure to high pH from, for example, sodium hydroxide. If any of these protein destroying steps are to be carried out, they must be completed, and all residual reagents be removed, before the growth factor(s) is added to the forming collagen matrix.

Presently, about twenty eight distinct collagen types have been identified in vertebrates, including bovine, ovine, porcine, chicken, marine, and human sources. Generally, the collagen types are numbered by Roman numerals, and the chains found in each collagen type are identified by Arabic numerals. Detailed descriptions of structure and biological functions of the various different types of naturally occurring collagens are generally available in the art.

The collagen may have the same composition as in naturally occurring sources. Examples of sources of collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen may further or alternatively comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the collagen is all type I or substantially all is collagen type I, namely, at least 60%, at least 65%, at least 70%, at least 75%, at least 80%, at least 85%, at least 90%, or at least 95%. In some embodiments all soft tissue growth factors are conserved. In other embodiments, at least 50%, at least 55%, at least 60%, at least 65%, at least 70%, at least 75%, at least 80% at least 85%, at least 90%, at least 95%, or at least 99% of the tissue growth factors are conserved.

The collagen may be from any collagen containing organ source such as skin, fascia, intestine, tendon, bladder and trachea. In some embodiments, human compatible collagen, and xenograft collagen can be used if they can be rendered non-immunogenic by a process that does not destroy the activity of the natural growth factors contained in the tissue or diminishes the activity by an acceptably small amount. Examples of processes that conserve natural growth factors include but are not limited to glycosidase digestion of carbohydrate moieties of the xenograft, which are optionally followed by treatment of carbohydrate moieties of the xenografts with a capping agent. Thus, sugars and other substances may be removed during processing, while the soft tissue growth factors remain associated with the collagen. In some embodiments soft tissue growth factors are conserved, but any sugars have been removed or at least 50%, at least 55%, at least 60%, at least 65%, at least 70%, at least 75%, at least 80% at least 85%, at least 90%, at least 95%, or at least 99% of them have been removed.

Self-Assembly of Collagen

The collagen can be made into a water-based dispersion by an acid treatment using techniques known to the art. As an example, a dispersion can include about 0.2 mL of lactic acid in 100 mL of distilled/de-ionized water with about 1.0 g of collagen (e.g., skin, tendon, fascia, ligament). In some embodiments, an acidic dispersion contains from about 0.1 wt % to about 3 wt % collagen, for example, from about 1 wt % (1 g collagen/100 mL solution) and 2 wt % collagen.

The collagen particles (e.g., macroscopic fibers, strands) in the dispersion are capable of self-assembly in the absence of a cross-linking agent.

Collagen has the ability to self-assemble into fibers, and this self-assembly has a significant role in maintaining the structure and the mechanical function of a given tissue. Collagen self-assembly occurs at a physiological pH where the assembled collagen fibers have identifiable quarter staggered configurations with alternating light and dark bands when observed under high magnifications. The regions where the collagen molecules overlap are the dark banding regions, while the staggered collagen molecules spanning from dark band to dark band are the light banding regions. Within the overlapping region, collagen molecules are bound together by native cross-links that are formed as part of fiber formation and overall molecule stabilization. Native cross-links alone are not the only element that is maintaining the stability of collagen molecules. Hydrogen bonding between these molecules can be facilitated by water that can also play a role in collagen self-assembly. Water may also continue to influence collagen stability after self-assembly on the micro- and macro-molecular level where water helps to maintain collagen molecular conformation and mechanical properties.

At a lower pH, collagen can disassemble into smaller fibril subunits. This physical transformation is termed swelling in acidic solutions. Without being bound by any particular theory, it is believed that the mechanism is made possible by the charges on the collagen protein becoming positive, which causes the collagen fibers to repel each other and deaggregate into subunits because the attractive forces of the interaction between triple helices are eliminated, which can result in a dispersion of insoluble collagen that is homogenous, opalescent, and optically isotropic.

In some embodiments, the dispersed collagen includes long fibers with diameters in the range of from about 0.05 μm to about 2.5 μm, and lengths from about 5 μm to about 100 μm. In various embodiments, the collagen fibers are macroscopic, that is they can be seen with the naked eye and their mean length of the collagen fibers is generally from about 3 to about 30 mm, in some embodiments, from about 5 to about 25 mm, and, in other embodiments, from about 7.5 to about 20 mm.

The process of deaggregation is reversible when the collagen dispersion is brought to physiological pH with evident collagen fiber assembly, e.g., if the acidity of the dispersion has been maintained above pH 3. As a result, in some embodiments, the pH of the collagen dispersion ranges from about 3 to about 6.5, for example, from about 3 to about 5, from about 3 to about 4.6, or about 4. As an example, about 0.2 mL of lactic acid in about 100 mL of water provides a pH from about 4 to about 5.

The methods of preparing the osteoimplant compositions involve using different collagen characteristics under different pH conditions to form the compositions. For example, bone particles, DBM or calcium phophates that are added to the acidic collagen dispersion slowly neutralize the dispersion as surface minerals from these sources are dissolved. The gradual rise in pH allows collagen assembly to take place around the bone particles, which may have exposed collagen fibers on their surfaces as a result of the mineral dissolution.

In various embodiments, the dispersion is very pure and collagen fibers can slowly be precipitated by drop-by-drop addition of an alkali, such as for example, sodium hydroxide, sodium carbonate, ammonia, sodium sulfate, or the like.

Typical pH for this precipitation step is about 7. The collagen fibers can be filtered or collected by hand or machine.

In various embodiments for the collagen precipitation, the pH of the acidic dispersion of collagen is pH of about 3.5 as a starting point for the precipitation reaction, at about pH of 4.6 transparent shard-like structures form, these structures precipitate out of the acid dispersion at a pH of about 6.0 to about 7.0, where they are transparent fully formed, firm and stable structures. In various embodiments, the temperature for precipitation is about 20 to about 30° C.

In various embodiments, the collagen formed is transparent shard-like structures resembling flexible icicles. The collagen fibers appear like shard-like gelatin because it is thought that water is trapped within the fiber structure. The collagen fibers can be de-watered making the fiber structure more textile like and allows further removal of contaminants, such as non-collagenous material, trapped within the water.

In various embodiments, dewatering of the collagen fibers can be accomplished by, for example, centrifugation, washing with suitable drying agents, air, and/or oven drying. Suitable drying agents include, for example, non-polar solvents such as for example, acetone, alcohol, or the like. Low temperature drying, such as by air and/or oven at temperatures, for example, of about 35 to about 40° C. can remove any remaining water as the solvents flash off, and can leave substantially pure collagen in dry firm fiber form.

Growth Factors

The growth factors include osteoinductive agents (e.g., agents that cause new bone growth in an area where there was none) and/or osteoconductive agents (e.g., agents that cause ingrowth of cells) and also fibrous or soft tissue inducing agents. Osteoinductive agents can be polypeptides or polynucleotide compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF, which may be specific for tendons and ligaments), Osteoprotegerin, Growth Differentiation Factors (GDFs), Cartilage Derived Morphogenic Proteins (CDMPs, which can be a foundation for soft or hard tissue), Lim Mineralization Proteins (LMPs), Platelet derived growth factor, (PDGF or rhPDGF, which is particularly advantageous for use with soft tissue), Insulin-like growth factor (IGF) or Transforming Growth Factor beta (TGF-beta) polynucleotides.

The collagen matrix may also comprise one or more additional growth factors, including but not limited to BMP-2, rhBMP12 or BMP7. These additional growth factors, unlike the conserved proteins are ones that have been added to the collagen during the formation of the collagen matrix and the matrix has these bioactive agents as part of its structure. The identity of proteins may be the same as or different than the conserved proteins. In some embodiments the collagen may be treated so that it also binds to these additional proteins. In some embodiments, the resulting concentration of growth factors is from 10% to 30% greater than in the natural state or from 30% to 50% greater than in the natural state or from 50% to 70% greater than in the natural state.

Additional growth factors can include polynucleotide compositions. Polynucleotide compositions include, but are not limited to, gene therapy vectors harboring polynucleotides encoding the osteoinductive polypeptide of interest. Gene therapy methods often utilize a polynucleotide that codes for the osteoinductive polypeptide operatively linked to or associated with a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide can be delivered in plasmid formulations. Plasmid DNA or RNA formulations refer to polynucleotide sequences encoding osteoinductive polypeptides that are free from any delivery vehicle that acts to assist, to promote or to facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties. Gene therapy vectors further comprise suitable adenoviral vectors including, but not limited to for example, those described in U.S. Pat. No. 5,652,224, which is herein incorporated by reference.

Additional growth factors also include but are not limited to isolated polynucleotides that encode Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents also include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that may be included within the collagen matrix are typically sterile. In a non-limiting method, sterility is readily accomplished for example by filtration through sterile filtration membranes (e.g., 0.2 micron membranes or filters). In one embodiment, the collagen matrix includes osteoinductive agents comprising one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same. In one embodiment, the at least one bone morphogenic protein is BMP-2.

BMPs utilized as osteoinductive agents may comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents that are included in the collagen matrix include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors that can be loaded in the collagen matrix further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents that can be loaded in the collagen matrix include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents that can be loaded in the collagen matrix include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents that can be loaded in the collagen matrix include one or more members of the family of Transforming Growth Factor-beta ("TGF-betas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents that can be loaded in the collagen matrix include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BCO30959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BCO28237 or AAH28237, as well as mature GDF-10 polypeptides or polynucleotides encoding the same. GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents that can be loaded in the collagen matrix include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents that can be loaded in the collagen matrix include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents that can be loaded in the matrix include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents that can be loaded in the collagen matrix are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

Other Additives

In various embodiments, the acidic collagen slurry can self-assemble upon addition of bone powder, calcium phosphate, hydroxyapatite, DBM or mixtures thereof. When added to the acidic collagen slurry, these compounds are all capable of raising the pH from about 5 to about 9, thereby causing the acidic collagen slurry to self-assemble into macroscopic collagen fibers forming the collagen matrix described herein. These bioactive agents are now part of the collagen matrix structure.

The matrices of the current application do not have the bioactive agent loosely associated with them. Rather, the bioactive agent is bound in the matrix and forms part of the matrix's structure.

In various embodiments, calcium phosphates can be used in forming the matrix. Calcium phosphate can be obtained from calcium phosphate ceramics. Examples of such calcium phosphate ceramics include calcium phosphate compounds and salts, and combinations thereof, including: tricalcium phosphate $Ca_3(PO_4)_2$ (TCP), including alpha-TCP, beta-TCP, and biphasic calcium phosphate containing alpha- and beta-TCP; amorphous calcium phosphate (ACP); monocalcium phosphate $Ca(H_2PO_4)_2$ (MCP) and monocalcium phosphate monohydrate $Ca(H_2PO_4)_2H_2O$ (MCPM); dicalcium phosphate $CaHPO_4$ (DCP) and dicalcium phosphate dihydrate $CaBPO_42H_2O$ (DCPD); tetracalcium phosphate $Ca_4(PO_4)\ _2O$(TTCP); octacalcium phosphate $Ca_8(PO_4)_4(HPO_4)_2.5H_2O$ (OCP); calcium hydroxyapatite $Ca_{10}(PO_4)_6(OH)_2$ (CHA); calcium oxyapatite $Ca_{10}(PO_4)_6O$ (COXA); calcium carbonate apatite $Ca_{10}(PO_4)_6CO_3$ (CCA); and calcium carbonate hydroxyapatites, e.g., $Ca_{10}(PO_4)_5(OH)(CO_3)_2$ and $Ca_{10}(PO_4)_4(OH)_2(CO_3)_3$ (CCHA).

Calcium phosphates useful herein also include calcium-deficient calcium phosphates in which the molar or mass ratio of Ca:P is reduced by about 20% or less, preferably about 15% or less, preferably about 10% or less, relative to the corresponding calcium non-deficient species, examples of which include calcium-deficient hydroxyapatites, e.g., $Ca_{10-X}(HPO_4)_X(PO_4)_{6-X}(OH)_{2-X}$ (0≤X≤1) (CDHA); calcium-deficient carbonate hydroxyapatites (CDCHA); calcium-deficient carbonate apatites (CDCA); and other calcium phosphate compounds and salts known as useful in the bone graft material field, e.g., calcium polyphosphates; and calcium-, phosphate-, and/or hydroxyl-"replaced" calcium phosphates, as further described below.

Calcium-replaced calcium phosphates are also useful herein, including homologs of any of the above in which some of, preferably a minority of (preferably about or less than: 40%, 35%, 33.3%, 30%, 25%, 20%, 15%, or 10%) the calciums are substituted with monovalent and/or divalent metal cation(s), e.g., sodium calcium homologs thereof, such as $CaNa(PO_4)$.

Phosphate-replaced calcium phosphates are also useful herein, including homologs of any of the above in which some of, preferably a minority of (preferably about or less than: 40%, 35%, 33.3%, 30%, 25%, 20%, 15%, or 10%) the phosphate groups are substituted with carbonate, hydrogen phosphate, and/or silicate groups.

Demineralized bone matrix (DBM) can also be useful to raise the pH of the acidic collagen slurry while the collagen matrix is forming the DBM can be used to raise the pH of the slurry from about 5 to about 9, thereby causing it to self-assemble into macroscopic collagen fibers forming the collagen matrix described herein.

DBM can be produced by acid extraction, thermal freezing, irradiation, or physical extraction of inorganic minerals from human or animal bone. The moisture level of the demineralized bone matrix can be easily controlled by air-drying or freeze-drying. Air dried demineralized bone matrix can include greater than about 10 weight percent of moisture, while in certain circumstances, freeze dried demineralized bone matrix can include less than about 6 weight percent of moisture. In some aspects, DBM can include between about 5 and about 30 weight percent (e.g., between about 5-20 weight percent, between about 10-15 weight percent, or between about 10-12 weight percent, or between about 5-10 weight percent) of moisture, e.g., water. In various embodiments, the demineralized bone matrix includes greater than or equal to about 6, 10, 12, 14, 16, 18, 20, 22, 24, 26, or 28 weight percent of moisture; and/or less than or equal to about 30, 28, 26, 24, 22, 20, 18, 16, 14, 12, or 6 weight percent of moisture. In some embodiments, the bone used to manufacture the demineralized bone matrix can be cortical, cancellous, cortico-cancellous of autogenous, allogeneic, xenogeneic or transgenic in origin.

In various embodiments of the present teachings, demineralized bone matrix can be supplied as powdered cortical or cancellous bone or dry chips ranging in size from about 10 μm to about 10 mm, from about 50 μm to about 5 mm, from about 100 μm to about 1 mm, from about 150 μm to about 0.8 mm, or from about 200 μm to about 0.75 mm.

If desired, the collagen matrix of this application can be modified in other ways. In addition to growth factors, any useful biological substance that is water soluble or at least hydrophilic can be added alone or in combination to the collagen as described above. The collagen should bind to one or more the sites of hydration on the water soluble or hydrophilic material and so displace the water. If the material is not naturally water soluble or hydrophilic, it can be derivatized or otherwise be made water soluble or hydrophilic before being combined with the collagen system. Types of useful water soluble/hydrophilic substances include, for example, antibiotics, pain relievers, growth factors, anti-inflammatories, etc.

Medically/surgically useful substances which can be readily combined with the collagen during its manufacture include, for example, bone fibers, hydroxyapatite, and soluble solids and/or liquids dissolved therein, for example, antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, peptides, vitamins, inorganic elements, inorganic compounds, cofactors for protein synthesis, hormones; endocrine tissue or tissue fragments; synthesizers; enzymes such as collagenase, peptidases, oxidases; polymer cell scaffolds with paraenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1) (IGF-2), platelet derived growth factor (PDGF), fibroblast growth factors (FGF), vascular endothelial growth factor (VEGF), angiogenic agents, bone promoters, cytokines, interleukins, genetic material, genes encoding bone promoting action, cells containing genes encoding bone promoting action; growth hormones such as somatotropin; bone digestors; antitumor agents; fibronectin; cellular attractants and attachment agents; immunosuppressants; permeation enhancers, for example, fatty acid esters such as laureate, myristate and stearate monesters of polyethylene glycol, surface active agents, enamine derivatives, α-keto aldehydes; nucleic acids; epidermal growth factor (EGF); all collagen types (not just type 1); non-collagenous proteins such as osteopontin, osteonectine, bone sialo proteins, vitronectin, thrombospondin, proteoglycans, decorin, biglycan, aggrecan, versican, tenascin, matrix gla protein hyaluronan; soluble and insoluble components of the immune system, soluble and insoluble receptors including truncated forms, soluble, insoluble and cell surface bound ligands including truncated forms; chemokines, bioactive compounds that are endocytosed; compounds capable of altering the membrane potential of cells, compounds capable of altering the monovalent and divalent cation/anion channels of cells; bone resorption inhibitors and stimulators; angiogenic and mitogenic factors; bioactive factors that inhibit and stimulate second messenger molecules; integrin adhesion molecules; clotting factors; externally expanded autograft or xenograft cells and any combinations thereof. The amounts of such optionally added substances can vary widely with optimum levels being readily determined in a specific case by routine experimentation.

Formation of an Implant

The collagen matrix containing a bioactive agent provided herein may be used to form an osteoinductive implant. The osteoimplant resulting from the mixture of the collagen matrix and/or bioactive agent, DBM, additive, may be flowable, have a putty consistency, may be shaped or molded, and/or may be deformable but it will not harden. The osteoimplant may assume a determined or regular form or configuration such as a sheet, plate, disk, tunnel, cone, or tube, to name but a few. Prefabricated geometry may include, but is not limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The osteoimplant can be machined or shaped by any suitable mechanical shaping means. Computerized modeling can provide for the intricately-shaped three-dimensional architecture of an osteoimplant custom-fitted to the bone repair site with great precision. In embodiments wherein the osteoimplant is shaped or moldable, the implant may retain coherence in fluids.

Accordingly, the osteoinductive collagen matrix may be subjected to a configuring step to form an osteoimplant. The configuring step can be employed using conventional equipment known to those skilled in the art to produce a wide variety of geometries, e.g., concave or convex surfaces, stepped surfaces, cylindrical dowels, wedges, blocks, screws, or the like. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof.

In some embodiments, the osteoinductive collagen matrix prepared from a mixture of collagen slurry and bioactive agent and DBM may be placed in a containment device such as a porous mesh to provide a delivery system. In various embodiments, the device may comprise a polymer (such as polyalkylenes (e.g., polyethylenes, polypropylenes, etc.), polyamides, polyesters, polyurethanes, poly(lactic acid-glycolic acid), poly(lactic acid), poly(glycolic acid), poly(glaxanone), poly(orthoesters), poly(pyrolicacid), poly(phosphazenes), L-co-G, etc.),other bioabsorbable polymer such as Dacron or other known surgical plastics, a natural biologically derived material such as collagen, a ceramic (with bone-growth enhancers, hydroxyapatite, etc.), PEEK (polyether-etherketone), dessicated biodegradable material, metal, composite materials, a biocompatible textile (e.g., cotton, silk, linen), or other. In one embodiment, the containment device is formed as a long bag-like device and may be used with minimally invasive techniques.

To facilitate on-site preparation and/or usage of the collagen matrix herein, the bioactive agent such as a growth factor, preferably in lyophilized or frozen form, and the collagen slurry, can be stored in separate packages or containers under sterile conditions and brought together in intimate admixture at the moment of use for immediate application to an osseous defect site employing any suitable means such as spatula, forceps, syringe, tamping device, or the like.

Alternatively, the collagen bioactive agent containing matrix can be prepared well in advance, lyophilized or otherwise dried and stored under sterile conditions until required for use. In some embodiments, the collagen matrix described herein can be combined with autograft bone marrow aspirate, autograft bone, preparations of selected autograft cells, autograft cells containing genes encoding bone promoting action prior to being placed in a defect site. In various embodiments, the implant composition is packaged already mixed and ready for use in a suitable container, such as for example, syringe, resealable non-toxic bottle, a bag mesh or pouch or is provided as a kit which can be prepared at a surgeon's direction when needed.

Having now generally described the invention, the same may be more readily understood through the following reference to the following examples, which are provided by way of illustration and are not intended to limit the present invention unless specified.

EXAMPLES

Example 1

In this example, collagen matrix containing a bone morphogenic protein (BMP) is prepared according to a method described herein and its BMP content is compared to that present in a collagen matrix where the BMP is added after the formation of the collagen matrix, similar to adding a BMP to a collagen sponge wherein the BMP has not chemically combined with the collagen matrix.

A collagen suspension is made from human collagen having been minimally processed and thus retains many immunogenic proteins. 1000 nanograms of lyophilized, water soluble BMP-2 is added to a 1% solution of suspended collagen (10 mg/I). The 1% collagen slurry is precipitated by combining it with 100 milligrams of hydroxyapatite powder. The collagen-hydroxyapatite precipitate is squeezed dry, and then rinsed with three 100 ml volumes of saline. After rinsing, the collagen-hydroxyapatite collagen matrix is dried and digested. The BMP-2 content of the collagen matrix is tested by ELISA assey.

By way of comparison, a control sample is also prepared. In the control sample, the same collagen-hydroxyapatite precipitate is formed without BMP-2 present. After squeezing it dry, BMP-2 is added to precipitate, which was then washed with 100 ml of saline, dried, and tested for BMP-2 by ELISA assey. The content of BMP-2 of the first sample is higher than that of the control sample.

Example 2

100 milligrams of hydroxyapatite is treated with 1000 nanograms of BMP-2 dissolved in water. The hydroxyapatite with added BMP-2 is dried. Subsequently the hydroxyapatite BMP-2 dried mixture is added to a collagen slurry and a precipitate with collagen or collagen matrix is formed as described in Example 1. After rinsing with 100 ml of saline, the resulting collagen matrix is analyzed for BMP-2 content by ELISA assey. The BMP-2 content is similar to the content of BMP-2 obtained from the first sample prepared in Example 1.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for making a biodegradable collagen matrix, the method comprising:
    providing an acidic collagen slurry;
    mixing at least one water soluble and/or hydrophilic bioactive agent with the acidic collagen slurry under conditions sufficient to cause the collagen slurry to self-assemble into macroscopic collagen fibers having a length from about 3 mm to about 30 mm, from about 5 mm to about 25 mm or from about 7.5 mm to about 20 mm and cause the at least one bioactive agent to form a collagen matrix containing the bioactive agent;
    adding an osteoclastogenesis inhibitor to the collagen matrix; and
    adding an osteoinductive additive comprising particulate demineralized bone matrix comprising bone chips,
    wherein the conditions sufficient to cause the collagen slurry to self-assemble comprise:
    (i) raising the pH of the slurry from 8 to about a pH of 9; or
    (ii) adding bone powder, calcium phosphate, hydroxyapatite, DBM or a mixture thereof to the slurry to raise the pH from 8 to about 9, and
    disposing the formed collagen matrix into a containment device comprising a biodegradable porous polymer mesh bag.

2. A method for making a biodegradable collagen matrix of claim 1, wherein the bioactive agent is uniformly distributed throughout the collagen matrix.

3. A method for making a collagen matrix of claim 1, wherein the at least one bioactive agent comprises a growth factor, a bone morphogenic protein, an analgesic, an anti-inflammatory, an antibiotic, a cytokine, a chemotherapeutic or a mixture thereof.

4. A method for making a collagen matrix of claim 3, wherein the at least one bone morphogenic protein is BMP-2.

5. A method for making a collagen matrix of claim 1, further comprising drying the collagen matrix after it is formed.

6. A method of making a collagen matrix of claim 5, wherein the collagen matrix is lyophilized prior to use.

7. A method for making a collagen matrix of claim 6, further comprising adding glycerol to the bioactive agent bearing collagen matrix prior to lyophilizing the matrix.

8. A method for making a collagen matrix of claim 1, wherein the collagen in the collagen slurry comprises mammalian type I, type, II, type III, type IV, type IX, type X, type XI and type XII collagen, and mixtures thereof.

9. A method for making a biodegradable collagen matrix of claim 1, wherein the collagen in the collagen slurry has not been treated for removal of immunogenic protein.

10. A method for making a collagen matrix of claim 1, wherein the collagen matrix forms a moldable composition that does not harden.

11. A method for making a biodegradable collagen matrix of claim 1, wherein the at least one water soluble and/or hydrophilic bioactive agent is a bone morphogenic protein, and the conditions sufficient to cause the collagen slurry to self-assemble comprise adding hydroxyapatite to the slurry to raise the pH from 8 to about 9.

12. A method for making a biodegradable collagen matrix, the method comprising:
    providing an acidic collagen slurry;
    adding a dried mixture of BMP-2 and hydroxyapatite to the acidic collagen slurry under conditions sufficient to cause the collagen slurry to self-assemble into macroscopic collagen fibers having a length from about 3 mm to about 30 mm, from about 5 mm to about 25 mm or from about 7.5 mm to about 20 mm and causing the BMP-2 to form a collagen matrix containing the BMP-2;
    adding an osteoclastogenesis inhibitor to the collagen matrix; and
    adding an osteoinductive additive comprising particulate demineralized bone matrix comprising bone chips,
    wherein the conditions sufficient to cause the collagen slurry to self-assemble comprise:

(i) raising the pH of the slurry from 8 to about a pH of 9; or
(ii) adding the hydroxyapatite to the slurry to raise the pH from 8 to about 9, and disposing the formed collagen matrix into a containment device comprising a biodegradable porous polymer mesh bag.

* * * * *